(12) United States Patent
Tseng et al.

(10) Patent No.: US 10,634,587 B2
(45) Date of Patent: Apr. 28, 2020

(54) SYSTEMS, METHODS AND COMPONENTS FOR ISOLATING CELLS FROM A FLUID SAMPLE

(71) Applicant: The Regents of the University of California, Oakland, CA (US)

(72) Inventors: Hsian-Rong Tseng, Los Angeles, CA (US); Mitch A. Garcia, Malibu, CA (US); Min Song, Los Angeles, CA (US); Libo Zhao, Los Angeles, CA (US); Shuang Hou, Los Angeles, CA (US); Tom Lee, Redondo Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/948,495

(22) Filed: Apr. 9, 2018

(65) Prior Publication Data

US 2018/0231441 A1 Aug. 16, 2018

Related U.S. Application Data

(63) Continuation of application No. 14/403,542, filed as application No. PCT/US2013/043171 on May 29, 2013, now abandoned.
(Continued)

(51) Int. Cl.
*G01N 1/28* (2006.01)
*B01L 9/00* (2006.01)
(Continued)

(52) U.S. Cl.
CPC ............... *G01N 1/28* (2013.01); *B01L 9/527* (2013.01); *G01N 1/286* (2013.01);
(Continued)

(58) Field of Classification Search
None
See application file for complete search history.

(56) References Cited

U.S. PATENT DOCUMENTS

| 2002/0037269 A1 | 3/2002 | Liotta et al. |
| 2005/0201901 A1 | 9/2005 | Grossman et al. |

(Continued)

FOREIGN PATENT DOCUMENTS

| CN | 101400778 A | 4/2009 |
| CN | 102405411 A | 4/2012 |

(Continued)

OTHER PUBLICATIONS

Adams et al., "Highly efficient circulating tumor cell isolation from whole blood and label-free enumeration using polymer-based microfluidics with an integrated conductivity sensor," J. Am. Chem. Soc., vol. 130, No. 27, pp. 8633-8641 (2008). [Cited in parent U.S. Appl. No. 14/403,542, filed Nov. 24, 2014.].
(Continued)

*Primary Examiner* — Erik B Crawford
(74) *Attorney, Agent, or Firm* — Venable LLP; Henry J. Daley; Miguel A. Lopez

(57) ABSTRACT

A system for isolating preselected cell types from a fluid sample that includes a plurality of cell types includes a cell-capture fluidic chip, and a chip holder configured to receive the cell-capture fluidic chip and to maintain the cell-capture fluidic chip with a substantially fluid-tight seal while in operation. The chip holder is further configured to release the cell-capture fluidic chip to be removed from the chip holder for further processing. The cell-capture fluidic chip includes a substrate, a laser micro-dissection membrane disposed on the substrate, and a channel-defining layer disposed on the laser micro-dissection membrane. The laser micro-dissection membrane has a surface adapted to capture preselected cell types preferentially over other cell types of
(Continued)

the plurality of cell types. The channel-defining layer is removable from the laser micro-dissection membrane for further processing of the cell-capture fluidic chip.

29 Claims, 12 Drawing Sheets

Related U.S. Application Data

(60) Provisional application No. 61/652,683, filed on May 29, 2012, provisional application No. 61/652,690, filed on May 29, 2012.

(51) Int. Cl.
*G01N 33/569* (2006.01)
*G01N 33/574* (2006.01)
*G01N 1/40* (2006.01)
*B01L 3/00* (2006.01)

(52) U.S. Cl.
CPC ..... *G01N 33/56966* (2013.01); *G01N 33/574* (2013.01); *B01L 3/502715* (2013.01); *B01L 3/502761* (2013.01); *B01L 2200/027* (2013.01); *B01L 2200/0647* (2013.01); *B01L 2300/0609* (2013.01); *B01L 2300/0816* (2013.01); *B01L 2300/0883* (2013.01); *G01N 1/4077* (2013.01); *G01N 2001/284* (2013.01); *G01N 2001/2886* (2013.01)

(56) References Cited

U.S. PATENT DOCUMENTS

| | | | |
|---|---|---|---|
| 2008/0113358 | A1 | 5/2008 | Kapur et al. |
| 2011/0045582 | A1 | 2/2011 | Lee et al. |
| 2012/0003711 | A1 | 1/2012 | Tseng et al. |

FOREIGN PATENT DOCUMENTS

| | | |
|---|---|---|
| WO | 2010/036912 A2 | 4/2010 |
| WO | 2010/108003 A2 | 9/2010 |
| WO | 2011/025976 A2 | 3/2011 |

OTHER PUBLICATIONS

International Preliminary Report on Patentability in International Patent Application No. PCT/US2013/043171, dated Dec. 2, 2014. [Cited in parent U.S. Appl. No. 14/403,542, filed Nov. 24, 2014.].
International Search Report and Written Opinion in International Patent Application No. PCT/US2013/043171, dated Sep. 4, 2013. [Cited in parent U.S. Appl. No. 14/403,542, filed Nov. 24, 2014.].
Kovac et al., "Intuitive, Image-Based Cell Sorting Using Opto-fluidic Cell Sorting," Anal. Chem. 2007, 79(24): 9321-9330. [Cited in parent U.S. Appl. No. 14/403,542, filed Nov. 24, 2014.].
Nagrath et al., "Isolation of rare circulating tumour cells in cancer patients by microchip technology," Nature, 2007, vol. 450, pp. 1235-1241. [Cited in parent U.S. Appl. No. 14/403,542, filed Nov. 24, 2014.].
Wang et al., "Highly efficient capture of circulating tumor cells by using nanostructured silicon substrates with integrated chaotic micromixers," Angewwandte Chemie International Edition, 2011, vol. 50, pp. 3084-3088. [Cited in parent U.S. Appl. No. 14/403,542, filed Nov. 24, 2014.].
Zheng et al., "3D microfilter devise for viable circulating tumor cell (CTC) enrichment from blood," Biomedical Microdevices, vol. 13, No. 1, pp. 203-213 (2011). [Cited in parent U.S. Appl. No. 14/403,542, filed Nov. 24, 2014.].
Bernards et al., "A progression puzzle," Nature 418. 823 (2002).
Criscitiello et al., "Circulating tumor cells and emerging blood biomarkers in breast cancer," Current Opinion in Oncology 22, 552-8 (2010).
Cristofanilli et al., "Circulating tumor cells, disease progression, and survival in metastatic breast cancer," The New England journal of medicine 351, 781-91 (2004).
Hou et al., "Polymer Nanofiber-Embedded Microchips for Detection, Isolation, and Molecular Analysis of Single Circulating Melanoma Cells," Angcw. Chem. Int. Ed. 52: 3379-3383 (2013), (Internal Cover Highlight).
Kaiser, "Medicine, Cancer's circulation problem," Science 327, 1072-4 (2010).
Li et al., "Electrospinning of polymeric and ceramic nanofibers as uniaxially aligned arrays," Nano Letters 3, 1167-1171 (2003).
Pantel et al., "Circulating tumour cells in cancer patients: challenges and perspectives," Trends in Molecular Medicine 16, 398-406 (2010).
Pantel et al., "Dissecting the metastatic cascade," Nature Reviews Cancer 4, 448-56 (2004).
Racila, et al., "Detection and characterization of carcinoma cells in the blood," Proceedings of the National Academy of Sciences of the United States of America 95, 4589-4594 (1998).
Sekine et al., "Functionalized conducting polymer nanodots for enhanced cell capturing: the synergistic effect of capture agents and nanostructures," Advanced Materials 23, 4788-92 (2011).
Tan et al., "Microdevice for the isolation and enumeration of cancer cells from blood," Biomedical Microdevices 11, 883-92 (2009).
Wang et al., "Three-dimensional nanostructured substrates toward efficient capture of circulating tumor cells," Angewandte Chemie International Edition 48, 8970-3 (2009).
Zhang et at. "Electrospun TiO2 Nanofiber-Based Cell Capture Assay for Detecting Circulating Tumor Cells from Colorectal and Gastric Cancer Patients," Advanced Materials 24, in press (2012).
Zhao et al., "High-Purity Prostate Circulating Tumor Cell Isolation by a Polymer Nanofiber-Embedded Microchip for Whole Exome Sequencing," Adv. Mater. 25: in press. (2013) (Internal Cover Highlight).
Zieglschmid, V., Hollmann, C. & Bocher, 0. Detection of disseminated tumor cells in peripheral blood. Critical Reviews in Clinical Laboratory Sciences 42, 155-96 (2005).

SYSTEMS, METHODS AND COMPONENTS FOR ISOLATING CELLS FROM A FLUID SAMPLE

CROSS-REFERENCE OF RELATED APPLICATION

This application is a Continuation of U.S. patent application Ser. No. 14/403,542, filed Nov. 24, 2014, which is a U.S. National Phase Application under 371 of International Patent Application No. PCT/US2013/043171, filed on May 29, 2013 which claims the benefit of U.S. Provisional Application No. 61/652,690, filed May 29, 2012 and U.S. Provisional Application No. 61/652,683, filed May 29, 2012, the entire contents of each of which are hereby incorporated by reference.

This invention was made with Government support under CA157396, awarded by the National Institutes of Health. The Government has certain rights in the invention.

BACKGROUND

1. Field of Invention

The field of the currently claimed embodiments of this invention relates to systems, methods and components for isolating cells from a fluid sample.

2. Discussion of Related Art

The most common causes of cancer-related death in patients occur when solid tumors metastasize. While the molecular mechanisms of cancer metastases are still largely unknown, there is a considerable body of evidence indicating that tumor cells are shed from a primary tumor mass at the earliest stages of malignant progression (Kaiser, J. Medicine. Cancer's circulation problem. *Science* 327, 1072-4 (2010); Bernards, R. & Weinberg, R.A. A progression puzzle. Nature 418, 823 (2002); Criscitiello, C., Sotiriou, C. & Ignatiadis, M. Circulating tumor cells and emerging blood biomarkers in breast cancer. *Current Opinion in Oncology* 22, 552-8 (2010)). These 'break-away' cancer cells enter the blood stream and travel to different tissues of the body as the cellular origin of metastases (Pantel, K. & Brakenhoff, R. H. Dissecting the metastatic cascade. *Nature Reviews Cancer* 4, 448-56 (2004)). The cells that escape from the primary tumor are known as circulating tumor cells (CTCs) (Pantel, K. & Alix-Panabieres, C. Circulating tumour cells in cancer patients: challenges and perspectives. *Trends in Molecular Medicine* 16, 398-406 (2010)). The gold standard for determining tumor status is through the histopathology analysis of biopsy samples. In early stage metastasis or recurrence, it is difficult to identify the metastatic/recurrence sites for biopsy.

CTCs can be regarded as the "liquid biopsy" of the tumor, thus providing convenient access to tumor cells, and earlier access to potentially fatal metastases. However, detection and characterization of CTCs have been technically challenging due to the extremely low abundance (a few to hundreds per mL) of CTCs among a high number ($10^9$ cells/mL) of hematologic cells (Racila, E., Euhus, D., Weiss, A. J., Rao, C., McConnell, J., Terstappen, L. W. M. M. & Uhr, J. W. Detection and characterization of carcinoma cells in the blood. *Proceedings of the National Academy of Sciences of the United States of America* 95, 4589-4594 (1998); Zieglschmid, V., Hollmann, C. & Bocher, 0. Detection of disseminated tumor cells in peripheral blood. *Critical Reviews in Clinical Laboratory Sciences* 42, 155-96 (2005)). It has been established that the variation of CTC number over the course of treatment period was found to be an independent predictor of therapeutic outcomes, progression-free and overall survival (Cristofanilli, M., Budd, G. T., Ellis, M. J., Stopeck, A., Matera, J., Miller, M. C., Reuben, J. M., Doyle, G. V., Allard, W. J., Terstappen, L. W. & Hayes, D. F. Circulating tumor cells, disease progression, and survival in metastatic breast cancer. The New England journal of medicine 351, 781-91 (2004)) of solid-tumor patients. Further, molecular analyses of these CTCs found in cancer patients may yield critical genomic, proteomic, or metabolomic information that could steer effective treatment of the cancer patient.

Although many technologies are available to immobilize CTCs, they lack the ability to isolate the single CTCs free from a background of non-specifically captured white blood cells (WBCs) for subsequent molecular and functional analysis (e.g., whole genome sequencing, RT-PCR). Therefore, there remains a need for improved devices and methods to isolate rare cells such as CTCs from whole blood and/or other bodily fluids.

SUMMARY

A system for isolating preselected cell types from a fluid sample that includes a plurality of cell types according to an embodiment of the current invention includes a cell-capture fluidic chip, and a chip holder configured to receive the cell-capture fluidic chip and to maintain the cell-capture fluidic chip with a substantially fluid-tight seal while in operation. The chip holder is further configured to release the cell-capture fluidic chip to be removed from the chip holder for further processing. The cell-capture fluidic chip includes a substrate, a laser micro-dissection membrane disposed on the substrate, and a channel-defining layer disposed on the laser micro-dissection membrane. The laser micro-dissection membrane has a surface adapted to capture preselected cell types preferentially over other cell types of the plurality of cell types. The channel-defining layer is removable from the laser micro-dissection membrane for further processing of the cell-capture fluidic chip. The cell-capture fluidic chip has an input port adapted to be connected to a fluid source and an output port to expel processed fluid such that the fluid sample flows from the fluid source through a fluid channel defined by the channel-defining layer over at least a portion of the surface of the laser micro-dissection membrane while in operation.

A chip holder for maintaining a cell-capture fluidic chip with a substantially fluid-tight seal while in operation according to an embodiment of the current invention includes a base component defining an indented region to accept the cell-capture fluidic chip therein, a press component configured to be placed over the cell-capture fluidic chip, and a clamp assembly configured to clamp the base component and the press component together so as to maintain a substantially fluidly tight seal during operation. The clamp assembly is further configured to unclamp to release the cell-capture fluidic chip for removal from the chip holder.

A cell-capture fluidic chip for capturing preselected cell types from a fluid sample that includes a plurality of cell types according to an embodiment of the current invention includes a substrate, a laser micro-dissection membrane disposed on the substrate, and a channel-defining layer disposed on the laser micro-dissection membrane. The laser micro-dissection membrane has a surface adapted to capture preselected cell types preferentially over other cell types of the plurality of cell types. The channel-defining layer is removable from the laser micro-dissection membrane for further processing of the cell-capture fluidic chip, and the cell-capture fluidic chip has an input port adapted to be connected to a fluid source and an output port to expel processed fluid such that the fluid sample flows from the fluid source through a fluid channel defined by the channel-defining layer over at least a portion of the surface of the laser micro-dissection membrane while in operation.

A method of isolating preselected cell types from a fluid sample that includes a plurality of cell types according to an embodiment of the current invention includes providing a cell-capture fluidic chip that includes a substrate, a laser micro-dissection membrane disposed on the substrate, and a channel-defining layer disposed on the laser micro-dissection membrane. The laser micro-dissection membrane has a surface adapted to capture preselected cell types preferentially over other cell types of the plurality of cell types. The method further includes providing the fluid sample such that it flows through a fluid channel defined by the channel-defining layer over at least a portion of the surface of the laser micro-dissection membrane to capture preselected cell types from the fluid sample, removing the channel-defining layer from the laser micro-dissection membrane and the substrate of the cell-capture fluidic chip after the providing the fluid sample, and performing laser micro-dissection on the laser micro-dissection membrane and the substrate of the cell-capture fluidic chip after the removing the channel-defining layer to collect preselected cell types captured from the fluid sample.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide systems and methods to immobilize CTC cells on a polymer-embedded microfluidic device. It can also include the use of laser micro-dissection (LMD) or laser capture micro-dissection (LCMD) techniques for isolation of single CTCs for subsequent molecular analysis, for example. This can be useful in medical hospitals for patient monitoring, pharmaceutical companies for drug efficacy studies in patients, and academic laboratories for research purposes, for example.

Figure 1:
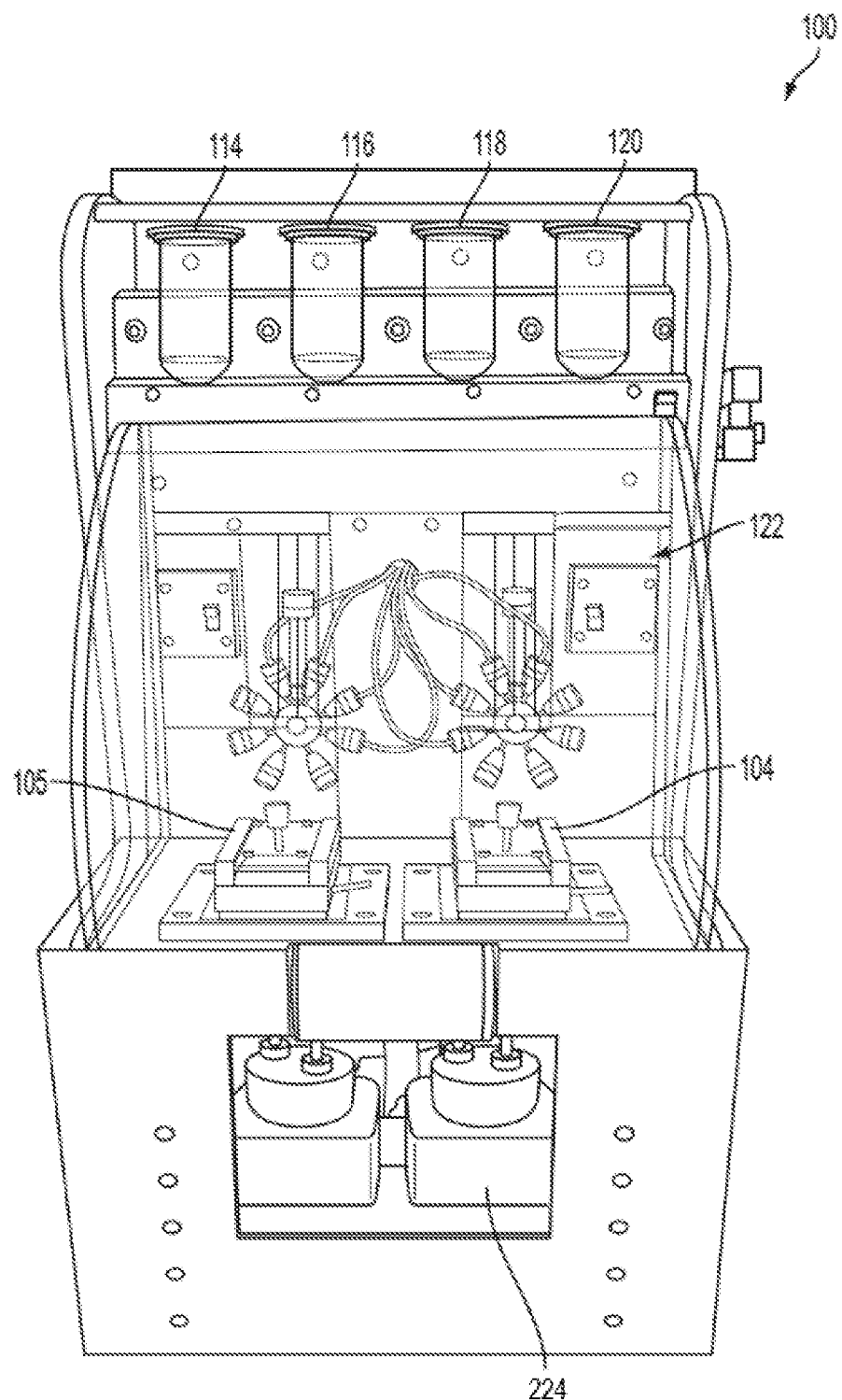
FIG. 1 shows a system for isolating preselected cell types from a fluid sample that has a plurality of cell types according to an embodiment of the current invention.
Figure 2A:
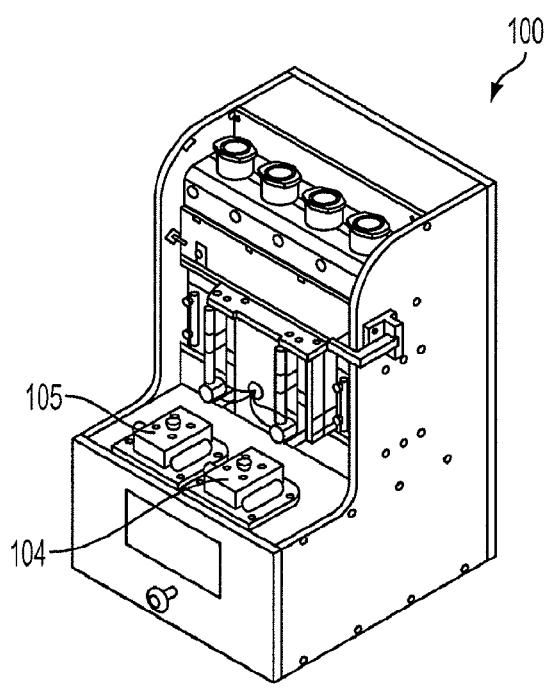
FIGS. 2A, 2B and 2C show a perspective view, a front view and a top view, respectively, of the system of FIG. 1.
Figure 2B:
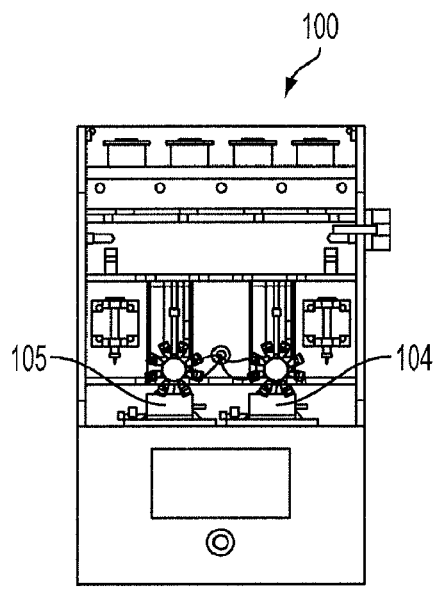
Figure 2C:
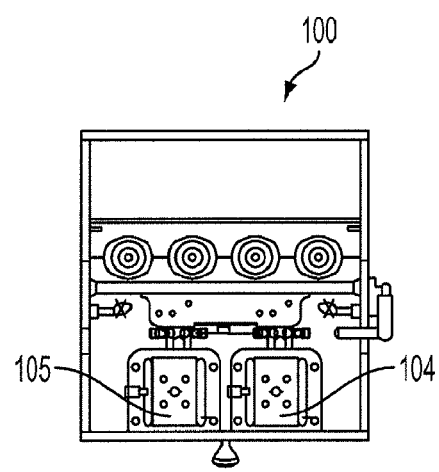

FIG. 1 provides an illustration of a system 100 for isolating preselected cell types from a fluid sample comprising a plurality of cell types. FIGS. 2A-2C show additional views of the system 100. The system 100 includes a cell-capture fluidic chip 102 (FIG. 3) and a chip holder 104 (see also, FIG. 4) configured to receive the cell-capture fluidic chip 102 and to maintain the cell-capture fluidic chip with a substantially fluid-tight seal while in operation. The chip holder 104 is further configured to release the cell-capture fluidic chip 102 to be removed from the chip holder 104 for further processing.

The system 100 also has a second chip holder 105. However, the concepts of the current invention are not limited to systems with any particular number of chip holders. There could be one, two, three, four or more chip holders according to various embodiments of the current invention. The cell-capture fluidic chip 102 (FIG. 3) includes a substrate 106, a laser micro-dissection membrane 108 disposed on the substrate 106, and a channel-defining layer 110 disposed on the laser micro-dissection membrane 108. The laser micro-dissection membrane 108 can be a single layer of material or can have two or more layers. In some embodiments, the laser micro-dissection membrane 108, regardless of whether it is one or more layers of material, has a surface 111 adapted to capture preselected cell types preferentially over other cell types of the plurality of cell types. The channel-defining layer 110 is removable from the laser micro-dissection membrane 108 for further processing of the cell-capture fluidic chip 102.

Figure 3:
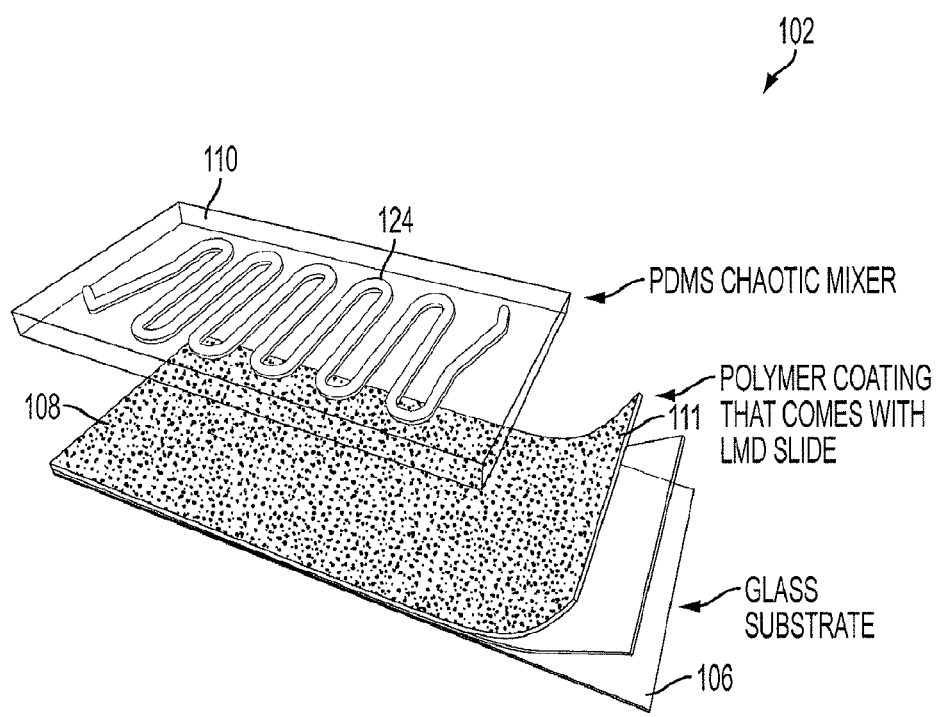
FIG. 3 is a schematic illustration of a cell-capture fluidic chip according to an embodiment of the current invention

In the example of FIG. 3, the cell-capture fluidic chip 102 has a glass substrate 106. However, the invention is not limited to only glass substrates. In addition, a convention laser micro-dissection slide that has a glass substrate and a laser micro-dissection membrane can be used according to some embodiments of the current invention. In this case, the upper surface (away from the substrate) can be modified and/or one or more layers of material can be deposited thereon to provide a desired surface 111 of the laser micro-dissection membrane 108. However, the broad concepts of the current invention are not limited to this example.

The cell-capture fluidic chip 102 has an input port 112 adapted to be connected to a fluid source (114, 116, 118 and/or 120) and an output port to expel processed fluid such that the fluid sample flows from the fluid source through a fluid channel 124 defined by the channel-defining layer 110 over at least a portion of the surface 111 of the laser micro-dissection membrane 108 while in operation.

In some embodiments, the channel-defining layer 110 can be, but is not limited to, a PDMS (polydimethylsiloxane) layer having a fluid channel 124 open on its lower side so as to come into contact with the surface 111 of the laser micro-dissection membrane 108. The fluid channel 124 can be a serpentine channel, for example, to increase an effective length of the channel and efficient usage of the surface 111, for example. When the channel-defining layer 110 is pressed together by the chip holder 104, a fluid-tight seal is formed so that fluid from a sample flows through the fluid channel 124 to expose the sample fluid to contact with the surface 111. The fluid channel 124 can have structures to cause turbulent flow (also referred to as a chaotic mixer) to avoid laminar flow. This can help increase the probability of the preselected cell types coming into contact with the surface 111. In some embodiments, the channel-defining layer 110 can be a thick PDMS structure, such as about 50 µm to 500 nm thick. In some embodiments, the channel-defining layer 110 can be substantially transparent to visible light to facilitate observation of and/or measurements of fluid flowing through the fluid channel 124.

The laser micro-dissection membrane 108 has at least one of a structural or chemical modification to capture preselected cell types preferentially over other cell types of the plurality of cell types. In some embodiments, the surface 111 of the laser micro-dissection membrane 108 can include a chemical modification to capture circulating cancer cells (CTCs) preferentially over other cell types of the plurality of cell types. In some embodiments, the surface 111 of the laser micro-dissection membrane 108 can include a polymer. The polymer can be deposited on a laser micro-dissection layer and/or can be part of a laser micro-dissection layer. In some embodiments, the polymer of the surface 111 can include at least one of Poly(Lactic-co-Glycolic Acid) (PLGA), Poly-CaproLactone (PCL), PolyLactide (PLA) or Chitosan (Poly-(D)glucosamine). In some embodiments, the polymer of the surface 111 can further include polyethylene glycol (PEG).

In some embodiments, the surface 111 can be a nanostructured surface. The term nanostructure is intended to include structures such as nanofibers, nanowires, nanoparticles, nanopillars, nanodisks, and other similar structures attached to, deposited on, or integral with the surface 111. The term nanostructure is intended to include structures that have at least two orthogonal dimensions that are less than 1 µm in some embodiments, less than 500 nm in some embodiments, less than 300 nm in some embodiments, less than 200 nm in some embodiments and equal to or greater than about 1 nm. For example, nanofibers, nanowires, and nanopillars could have a length greater than 10 µm, in some cases much greater than 1 µm, but their cross-sectional dimensions are nanoscale.

In some embodiments, the surface 111 can include polymer nanofibers deposited on the surface. The polymer nanofibers can be formed as at least part of the surface 111 by electrospinning or nanoimprinting, for example. However, the broad concepts of the current invention are not limited to these examples.

In some embodiments, the surface 111 can include at least one CTC capture agent attached to a polymer coating, for example. In some embodiments, the CTC capture agent can be attached to the polymer coating by at least one of biotin or streptavidin conjugation, for example. The CTC capture agent can include, but is not limited to, at least one of EpCAM, CA19-9, CD146, or CD147 antibodies.

In some embodiments, the surface 111 can have a chemical modification to capture fetal nucleated red blood cells (fNRBCs) from maternal blood preferentially over other cell types of said plurality of cell types. The chemical modification can include attaching at least CD71 and CD147 antibodies to the surface 111.

In some embodiments, the system 100 can be used for isolating rare cells from bodily fluids and dissociated tissue, for example. When anti-EpCAM is grafted on polymer substrates, the substrates can be employed to capture breast cancer cells from ascitic fluid collected from a metastatic breast cancer patient, for example. When anti-CA19-9 is grafted on the polymer substrates, the substrates can be employed to capture pancreatic cancer cells from dissociated pancreatic cancer tissue (containing about 10% of cancer cells and 90% of stromal cells), for example. In some embodiments, single pancreatic cancer cells can be isolated for subsequent molecular and functional analysis. When a cocktail antibody reagent (e.g., anti-CD71 and anti-CD147) is grafted on the polymer substrates, the substrates can be employed to capture fetal nucleated red blood cells (fNRBCs) from maternal blood at 6-15 week of pregnancy, for example. Again, single fNRBCs can be isolated by LCM techniques for downstream analysis, for example. However, the broad concepts of the current invention are not limited to these examples.

In some embodiments, the system 100 can further include a fluid supply and control assembly 122 adapted to be fluidly connected to the cell-capture fluidic chip 102 while being held by the chip holder 104. The fluid supply and control assembly 122 can include the fluid sources 114, 116, 118 and/or 120, for example. In some embodiments, the fluid supply and control assembly 122 can further include one or more waste containers, such as waste container 224. The chip holder 104 (or holders, depending on how many are desired for use in parallel) can be further configured, along with the fluid supply and control assembly 122 to be attachable and removable therefrom to facilitate processing and handling.

In some embodiments, the fluid supply and control assembly 122 can be a highly efficient blood processing device for the capture of rare cells from blood samples onto the surface 111. However, other fluid samples can also be used. It can also serve several functions in some embodiments, such as being used to test for leaks in the chip holder 104, precise loading and running of fluid samples, and fixation of immobilized cells onto the surface 111 of the laser micro-dissection membrane 108. The components of the fluid supply and control assembly 122 can include two eight-valve Hamilton PSD/3 syringe pumps, four top loaded fluid reservoirs (114, 116, 118, 120), two 1-mL syringe tubes for blood sample loading, two waste containers, surgical grade valve connectors and plastic tubing, for example. However, the broad concepts of the current invention are not limited to this example. In some embodiments, fluid supply and control assembly 122 can have dimensions such that it can fit on top of a laboratory bench top while still occupying a small footprint. Some advantages of the fluid supply and control assembly 122 can include automation of rare cell isolation and avoidance of human error from blood handling.

Figure 4A:
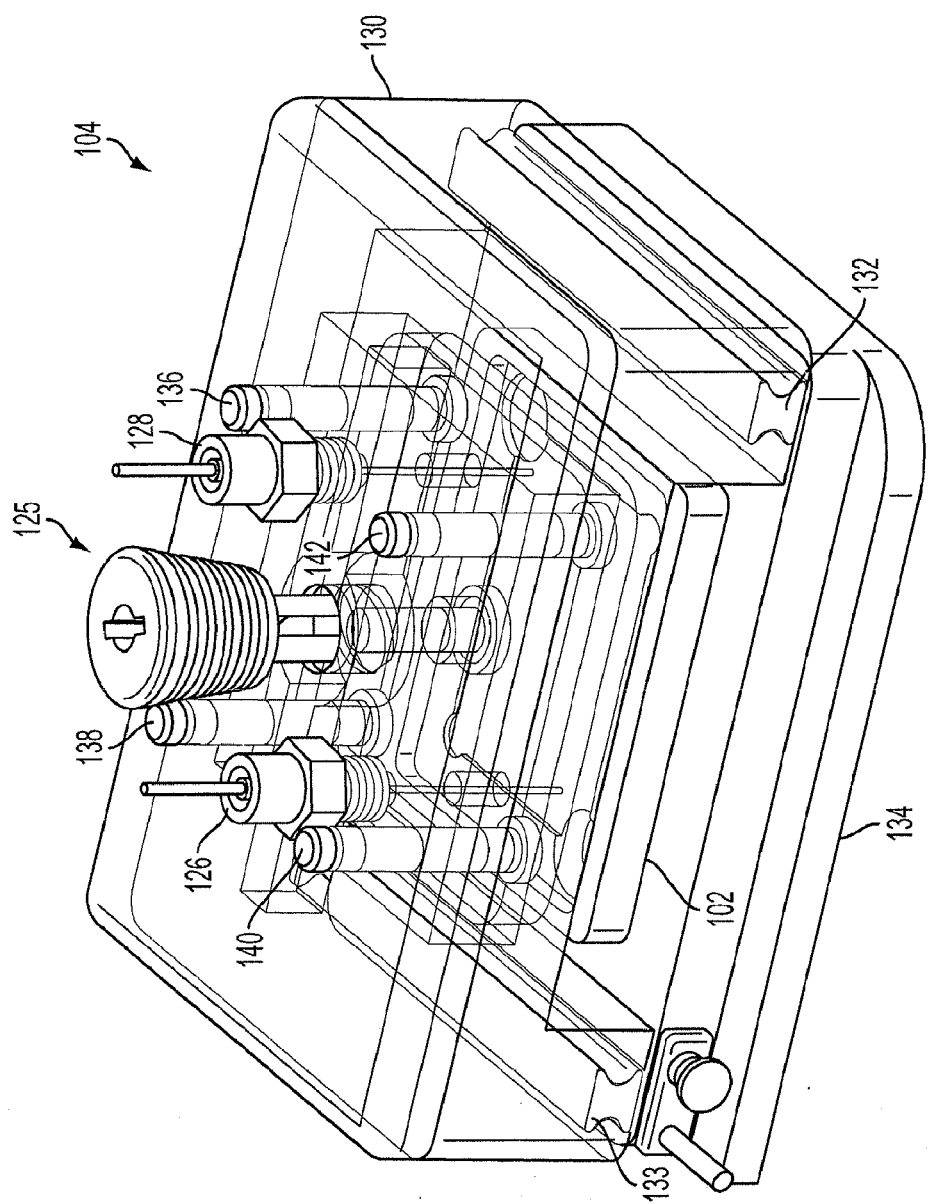
FIG. 4A is an illustration of a chip holder according to an embodiment of the current invention.

FIG. 4A shows a more detailed view of the chip holder 104. The cell-capture fluidic chip 102 is shown loaded and clamped within the chip holder 104. The chip holder is specifically designed to evenly press the channel-defining layer 110 against the laser micro-dissection membrane 108 to ensure that no leaks occur when running a fluid sample through the device.

The chip holder 104 has a turn-locking mechanism 125 where the pressure is increased gradually and does not require the user to apply much force as needed other mechanisms. The inlet and outlet for the chip holder 104 that has a cell-capture fluidic chip 102 loaded therein is also designed to be user-friendly. The inlets and outlets (126, 128) are sealed to the fluid supply and control assembly 122 by turning the complementary connector tubes. Other embodiments require one to poke connector tubes into the device. In addition, the chip holder 104 can also include alignment markers for precise placement of channel-defining layer 110 over laser micro-dissection membrane 108. The chip holder 104 has slide-in mechanism that allows for almost effortless assembly of the top-piece 130 of the chip holder 104 to slide along the rails (132, 133) of the bottom-piece 134. It also has four spring assemblies (136, 138, 140, 142) that press down at the corners of the channel-defining layer 110 to ensure a tight seal is formed between the channel-defining layer 110 and the laser micro-dissection membrane 108.

Figure 4B:
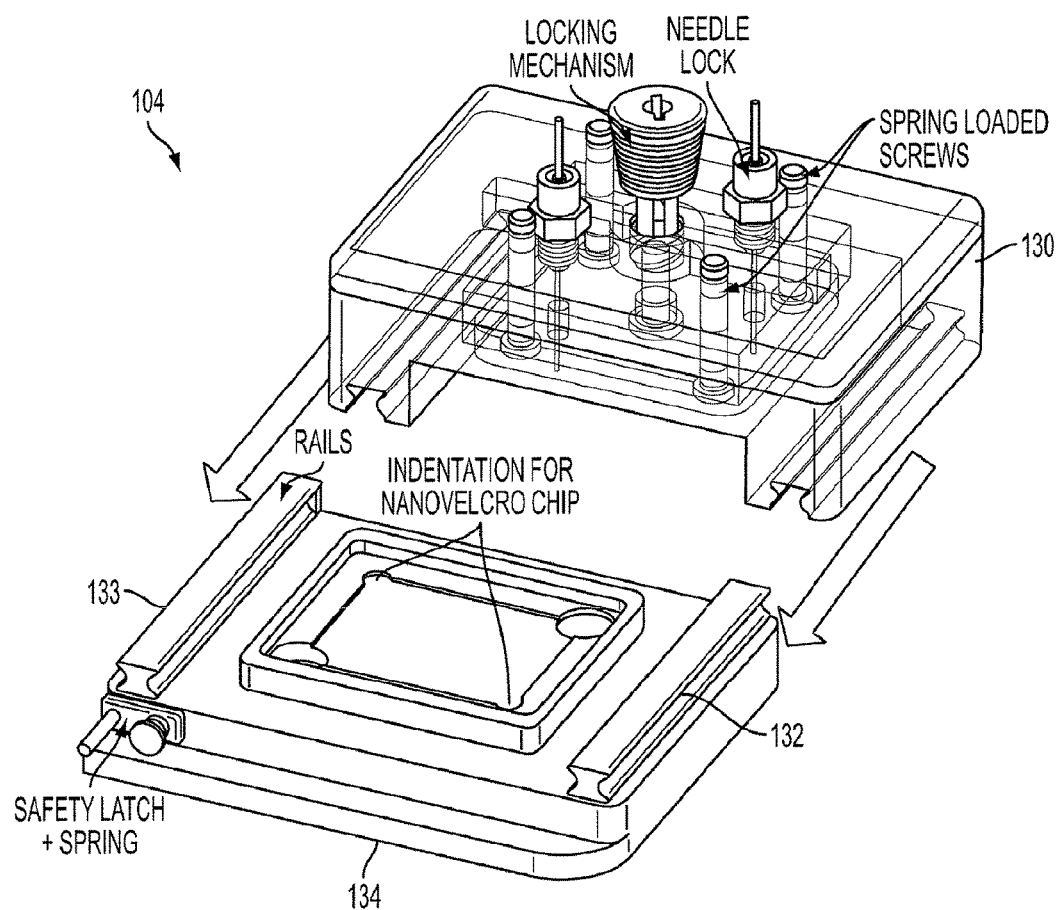
FIG. 4B is another illustration of the chip holder of FIG. 4A, but in a configuration ready for loading a cell-capture fluidic chip.

FIG. 4B shows the chip holder of FIG. 4A, but with the top and bottom sections removed as would be the configuration for loading cell-capture fluidic chip 102. In this example, the cell-capture fluidic chip 102 is referred to as a NanoVelcro chip. In some embodiments, the chip holder 104 can have a safety latch to ensure that once the chip holder 104 is assembled it cannot disassemble by accidental bumps by a human operator. The bottom-piece 134 also has an indentation that is specifically designed to fit the NanoVelcro substrates, and has a broader indentation for precise alignment of the channel-defining layer 110 over the NanoVelcro substrate. The top-piece uses a screw-in mechanism that slowly applies equal pressure from the spring-loaded screws to the channel-defining layer 110 to ensure a tight leak-proof seal is formed with the NanoVelcro substrates. Additionally, the top-piece 130 also can have connector tubes that utilize a needle-locks in order to quickly connect the chip holder 104 to the fluid supply and control assembly 122.

Figure 5C:
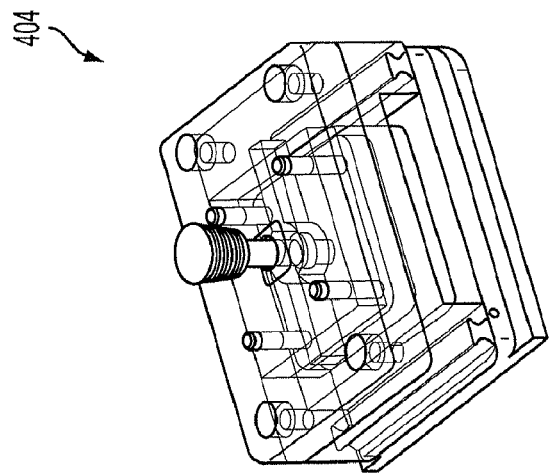
FIGS. 5A-5C shows some alternative embodiments of chip holders.
Figure 5B:
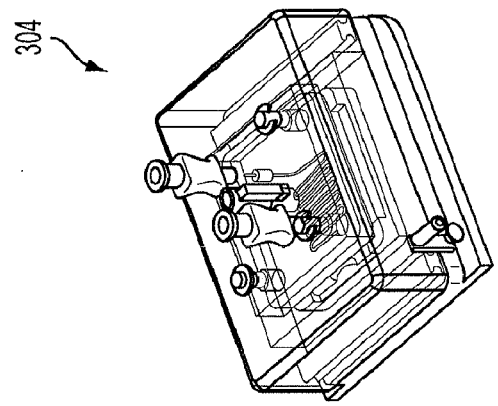
Figure 5A:
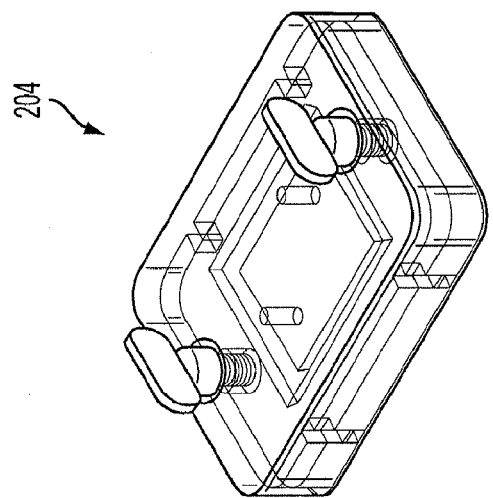

FIGS. 5A-5C are illustrations of alternative embodiments (204, 304, 404, respectively) of chip holder 104. However, the chip holder 204 requires the user to apply significant force to tighten the screws to ensure the device was properly sealed. The chip holder 304 has a click-on locking mechanism that does not require as much strength as chip holder 204, but the clicking mechanism sometimes can break the laser micro-dissection membrane 108 and/or substrate 106 due to the sudden instantaneous pressure it applies. The chip holder 404 is similar to chip holder 104, but does not include the improved inlets and outlets (126, 128) for connecting to the fluid supply and control assembly 122.

Some embodiments of the current invention can include conventional laser micro-dissection components such as infrared and/or ultraviolet lasers, for example.

EXAMPLES

The following examples help explain some concepts of the current invention. However, the general concepts of the current invention are not limited to the particular examples.

Some embodiments of the current invention can provide the ability to immobilize CTCs onto a polymer substrate for subsequent single cell CTC isolation with either a laser micro-dissection instrument (i.e., utilizing a high powered UV embedded laser for cutting) or a laser capture micro-dissection (i.e., utilizing a solid-state IR laser to gently embed cells into a gel which preserves the biomolecular integrity of the cells components) or their combination. Currently, there is no existing systems and methods that can accomplish both CTC immobilization and isolation with high efficiency and with good cell viability for subsequent molecular analysis. Some embodiments of the current invention can enable clinicians to dynamically record a tumor's progression/evolution by collecting CTCs from a cancer patient over the course of treatment, for example. A thorough understanding and knowledge of how a tumor has evolved resistance to a drug, at the genetic/transcription level, can provide insight into the design of better drugs to inhibit cancer proliferation Immobilize CTCs onto a polymer substrate. CTCs are often found in small abundance (due in part to poor CTC capture performance) and have poor sample purity (due to non-specific capture of WBCs) which has limited their use in molecular analysis approaches (e.g., sequencing and RT-PCR).

Figures 6A, 6B, 6C, 6D, 6E, 6F, 6G:
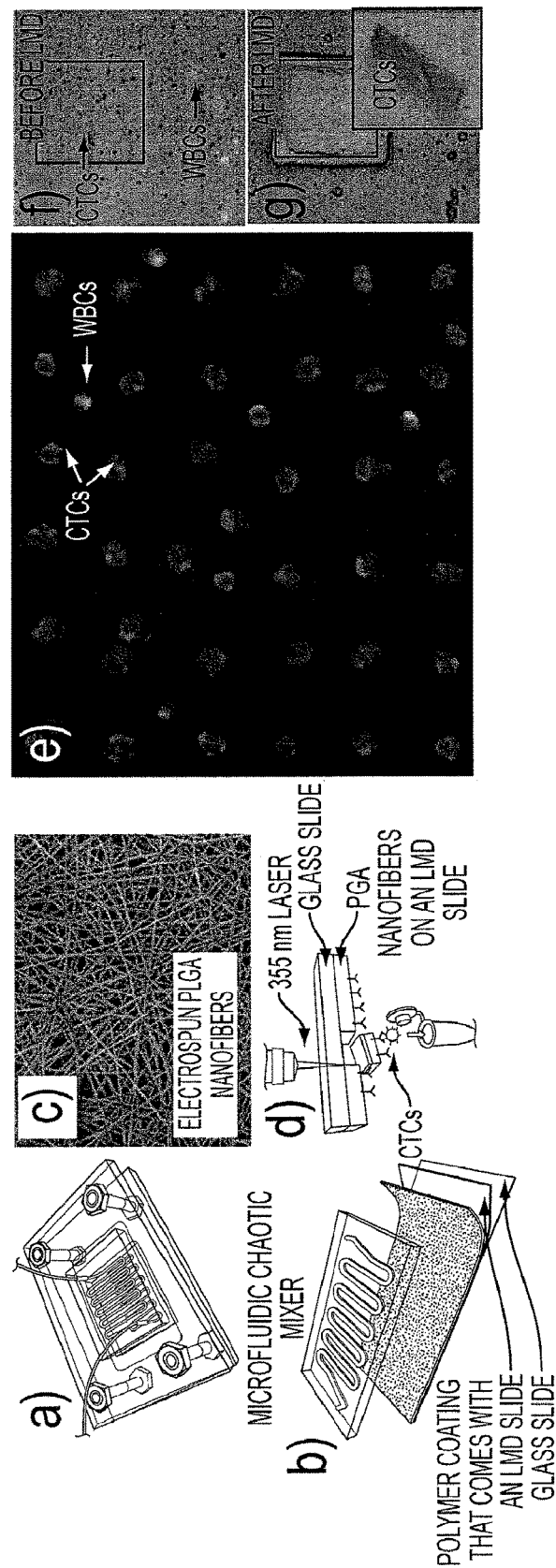
FIGS. 6A-6G help illustrate an example of an embodiment of the current invention. a) Blood sample flowing through the NanoVelcro CTC Chip. b) The device includes an overlaid microfluidic chaotic mixer and a transparent NanoVelcro substrate (prepared by depositing electrospun PLGA nanofibers onto a LIVID slide). c) An SEM image shows the morphologies of horizontally packed ultra-long PLGA nanofibers (with diameter of ca. 100 nm). d) The transparent NanoVelcro substrate with immobilized CTCs can be coupled to a laser microdissection or a laser capture microdissection instrument for single cell isolation. e) NanoVelcro CTC Chip with 45 CTCs isolated from 1-mL of blood collected from a metastatic cancer patient. f) CTCs immobilized on a transparent NanoVelcro substrate. g) By using LIVID technique, single CTCs were isolated on the dissected substrates (inset).

FIGS. 6A-6C show an example of an embodiment of the current invention. In this example, the laser micro-dissection membrane 108 and substrate 106 will be referred to as a transparent NanoVelcro substrate. It is based on electrospun Poly(Lactic-co-Glycolic Acid) (PLGA) polymer and has nanofibers that can be used to immobilize CTCs (see FIGS. 6B and 6C). By using conjugation chemistry (Wang, S., Wang, H., Jiao, J., Chen, K. J., Owens, G. E., Kamei, K., Sun, J., Sherman, D. J., Behrenbruch, C. P., Wu, H. & Tseng, H. R. Three-dimensional nanostructured substrates toward efficient capture of circulating tumor cells. *Angewandte Chemie International Edition* 48, 8970-3 (2009); Sekine, J., Luo, S. C., Wang, S., Zhu, B., Tseng, H. R. & Yu, H. H. Functionalized conducting polymer nanodots for enhanced cell capturing: the synergistic effect of capture agents and nanostructures. *Advanced Materials* 23, 4788-92 (2011)), cancer specific capture agents can be introduced onto the transparent NanoVelcro substrate for capturing CTCs from whole blood samples with superb efficiency. A 3-color ICC protocol for parallel staining of cells immobilized onto the transparent NanoVelcro substrate allows for unambiguous identification of CTCs from a background of WBCs (see FIGS. 6E and 6F) and other cellular debris.

Figure 7:
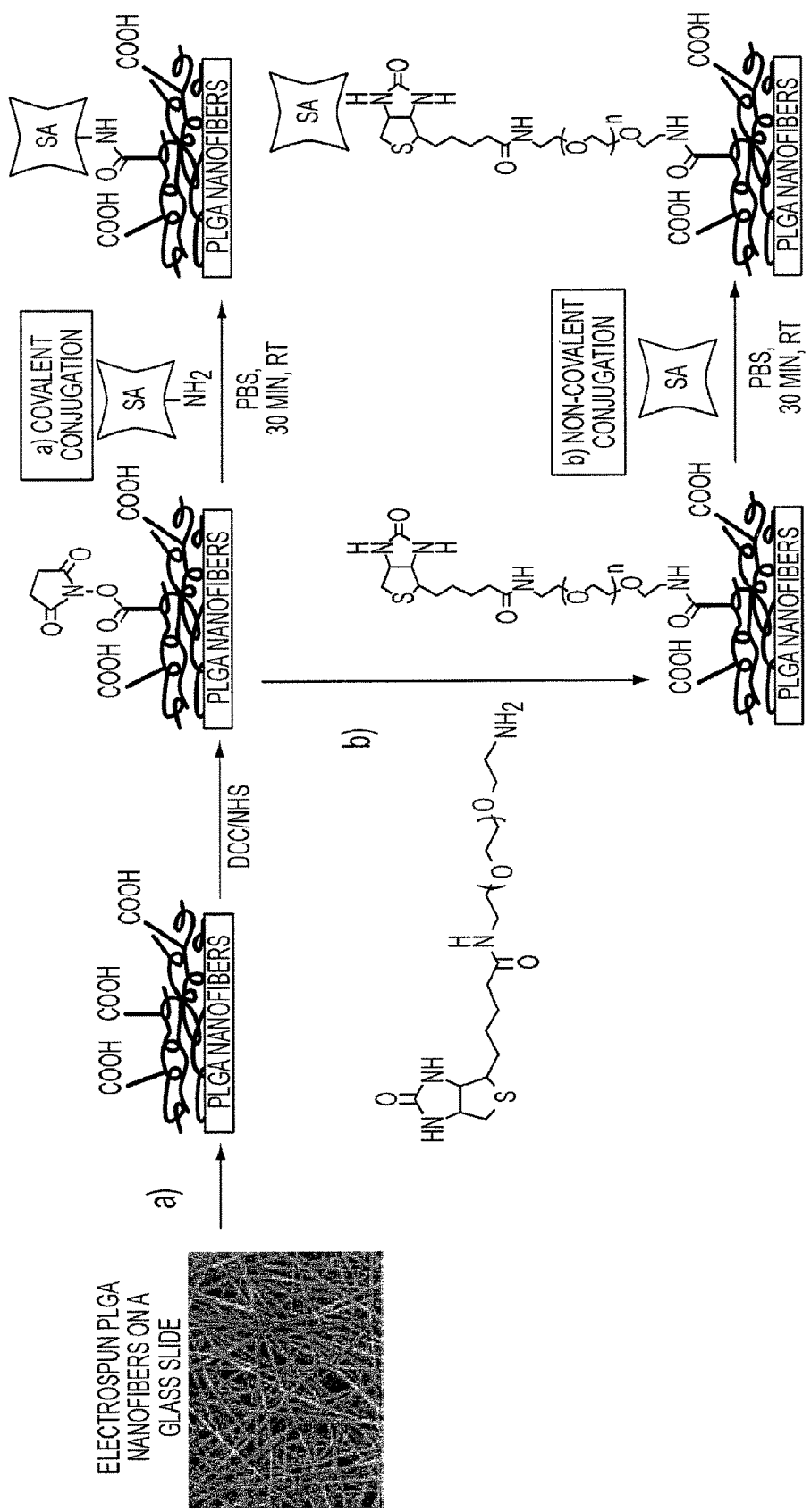
FIG. 7 is a schematic representation that summarizes a) the covalent conjugation approach for introducing streptavidin coating onto the PLGA nanofibers embedded in transparent NanoVelcro substrates; and b) an alternative surface modification approach for introducing anti-biofouling PEG group onto the NanoVelcro Substrates in order to suppress non-specific capture of WBCs and enhance stability of NanoVelcro substrates for long-term storage and convenient shipping.

Polymer Enrichment Assay. Transparent NanoVelcro substrates are prepared by depositing PLGA nanofibers onto an LMD membrane slide using an electrospinning setup as reported in the literature (Zhang, N., Deng, Y., Tai, Q., Cheng, B., Zhao, L., Shen, Q., He, R., Hong, L., Liu, W., Guo, S., Liu, K., Tseng, H.-R., Xiong, B. & Zhao, X.-Z. Electrospun TiO2 Nanofiber-Based Cell Capture Assay for Detecting Circulating Tumor Cells from Colorectal and Gastric Cancer Patients. *Advanced Materials* 24, in press (2012); Li, D., Wang, Y. L. & Xia, Y. N. Electrospinning of polymeric and ceramic nanofibers as uniaxially aligned arrays. *Nano Letters* 3, 1167-1171 (2003)). The process begins by preparing a 5% PLGA polymer solution in acetonitrile and then placing it into a stainless steel needle for electrospinning. During the electrospinning deposition, the PLGA polymer solution is injected via a syringe pump, and a high-voltage DC power is applied between the needle and a metal substrate located behind the LMD membrane slide. By controlling the time employed for depositing PLGA nanofibers, the density of nanofibers on the LMD membrane slide can therefore be controlled. Through a series of studies (Sekine, J., Luo, S. C., Wang, S., Zhu, B., Tseng, H. R. & Yu, H. H. Functionalized conducting polymer nanodots for enhanced cell capturing: the synergistic effect of capture agents and nanostructures. *Advanced Materials* 23, 4788-92 (2011)), we identified that 10-min deposition time yields horizontally packed ultra-long PLGA nanofibers (Zhang, N., Deng, Y., Tai, Q., Cheng, B., Zhao, L., Shen, Q., He, R., Hong, L., Liu, W., Guo, S., Liu, K., Tseng, H.-R., Xiong, B. & Zhao, X.-Z. Electrospun TiO2 Nanofiber-Based Cell Capture Assay for Detecting Circulating Tumor Cells from Colorectal and Gastric Cancer Patients. *Advanced Materials* 24, in press (2012)) with suitable density to achieve optimal CTC capture performance. The surface chemistry (i.e., direct conjugation of streptavidin onto PLGA nanofibers) will be conducted following the earlier procedure (Wang, S., Wang, H., Jiao, J., Chen, K. J., Owens, G. E., Kamei, K., Sun, J., Sherman, D. J., Behrenbruch, C. P., Wu, H. & Tseng, H. R. Three-dimensional nanostructured substrates toward efficient capture of circulating tumor cells. *Angewandte Chemie International Edition* 48, 8970-3 (2009))[3][3] (i.e., see FIG. 7).

Laser Microdissection and Laser Capture Microdissection Techniques. Our laser microdissection technique according to an embodiment of the current invention uses a UV laser to isolate specifically identified CTCs from the transparent NanoVelcro substrate. After the laser cuts out the region containing CTCs, they fall into a small volume tube by the action of gravity. Thus, this method provides a fast and reliable contact-free and contamination-free method for CTC collection. The laser capture microdissection technique utilizes a solid-state IR laser to gently capture single CTCs onto a gel cap. Thus, this capturing method is a gentle approach that can protect the biomolecular integrity of the CTCs. Finally, the laser microdissection and laser capture microdissection techniques are compatible methods, meaning they can be used together as needed.

Additional examples and data can be seen in S. Hou, Q. Shen, L. Zhao, J. Yu, C. Ng, X. Kong, D. Wu, M. Song, X. Shi, X. Xu, W.-H. OuYang, R. He, X.-Z. Zhao, B. Xiong, T. Lee, C. Brunicardi, M. A. Garcia, A. Ribas, R. S. Lo, H.-R. Tseng (2013) Polymer Nanofiber-Embedded Microchips for Detection, Isolation, and Molecular Analysis of Single Circulating Melanoma Cells. Angew. Chem. Int. Ed. 52: 3379-3383. (Internal Cover Highlight); and L. Zhao, Y.-T. Lu, F. Li, K. Wu, S. Hou, J. Yu, Q. Shen, D. Wu, M. Song, W.-H. OuYang, Z. Luo, T. Lee, C. Shao, X. Xu, M. A. Garcia, L. W. K. Chung, M. Rettig, H.-R. Tseng, E. M. Posadas (2013) High-Purity Prostate Circulating Tumor Cell Isolation by a Polymer Nanofiber-Embedded Microchip for Whole Exome Sequencing, Adv. Mater. 25: in press. (Internal Cover Highlight), the entire contents of which are incorporated herein by reference.

Figure 8A:
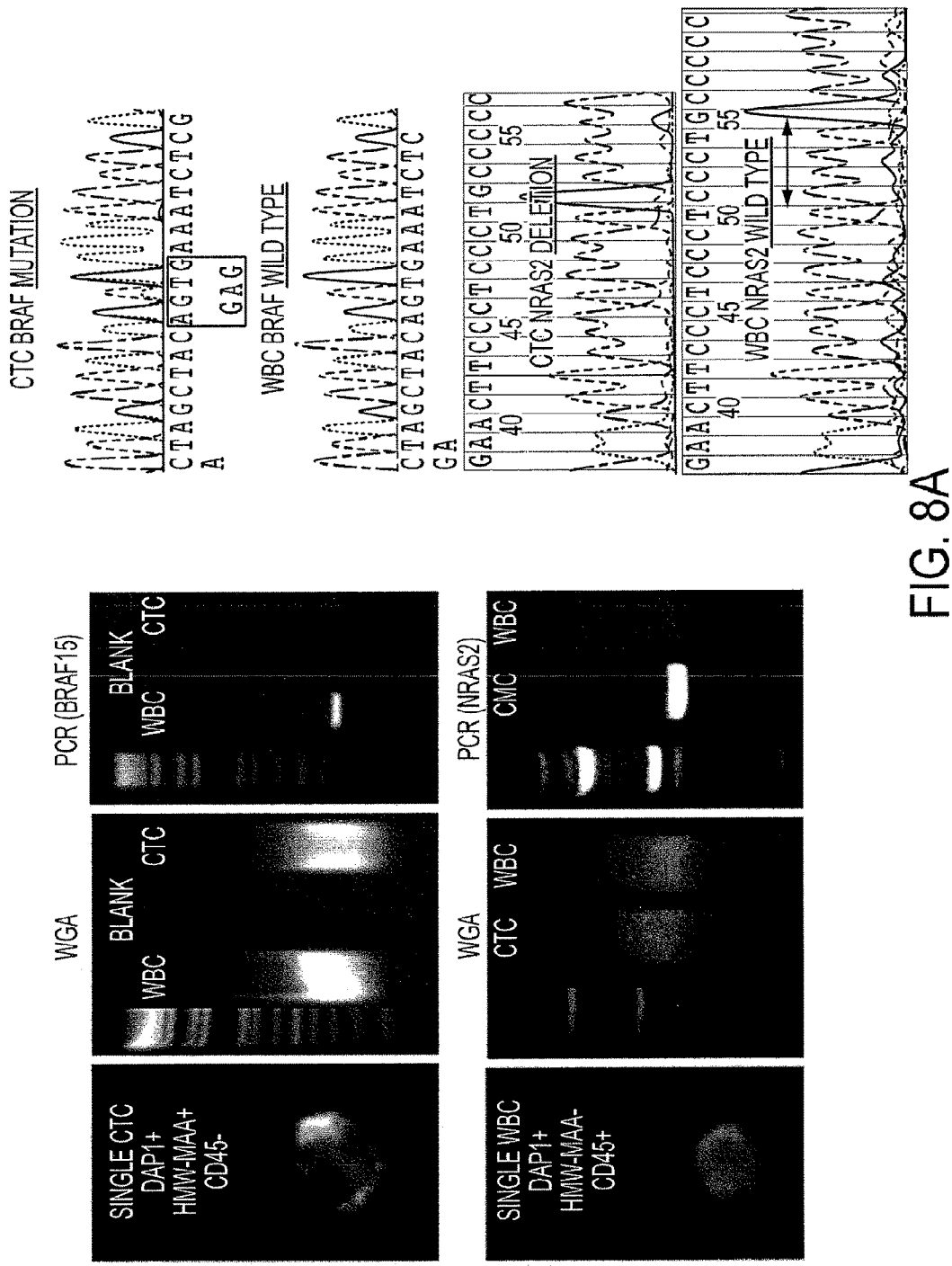
FIG. 8A shows single CTCs and WBCs were captured and isolated from a melanoma patient's blood samples according to an embodiment of the current invention. After PCR amplification, $BRAF^{V600E}$ mutation and NRAS deletion in intron (37bp 3' of NRAS exon 2; nucleotides CCCT deleted) were detected. Here WBCs were employed as control samples (Wild Type).
Figure 8B:
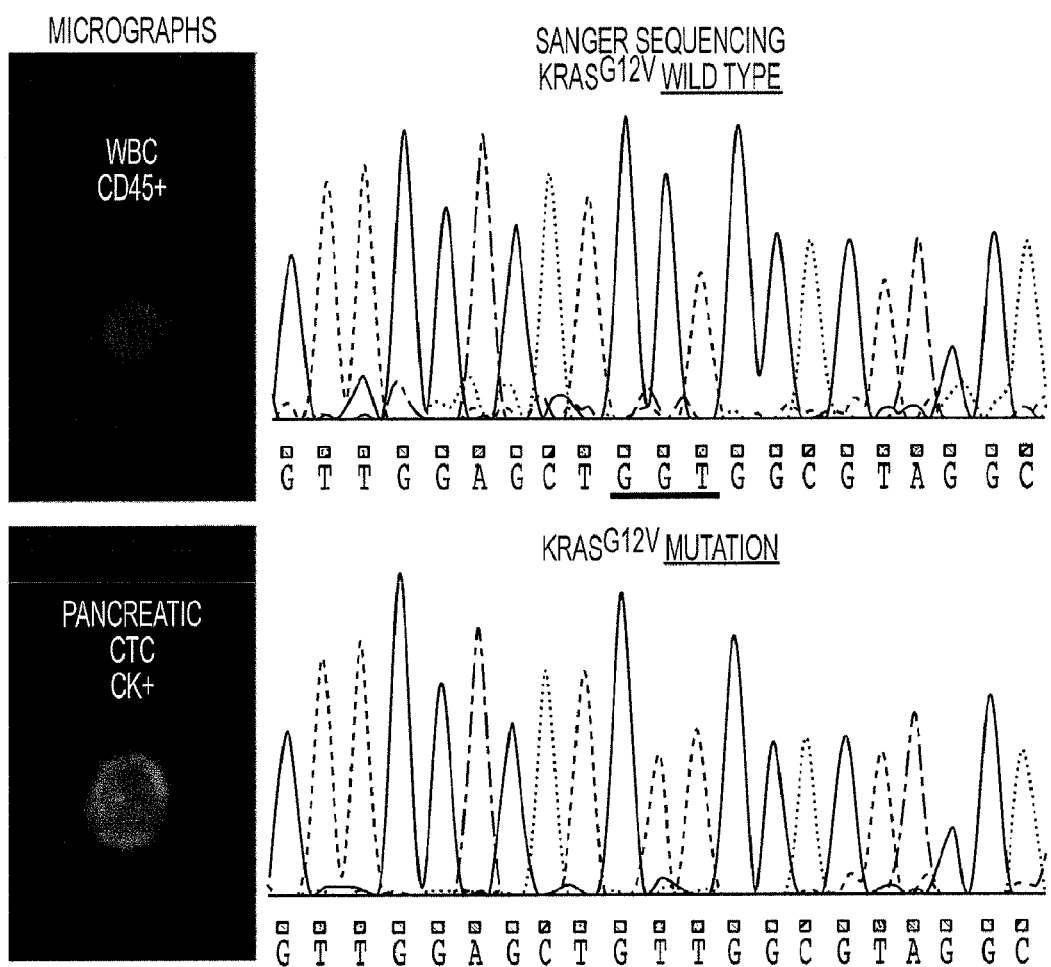
FIG. 8B Shows data on KRAS mutation detection using CTCs isolated form pancreatic cancer patients. A commonly found $KRAS^{G12V}$ mutation was detected in 19 out of the 20 CTCs, and wild type KRAS in WBCs. It is noteworthy that the Sanger sequencing data obtained for both $BRAF^{V600E}$ (melanoma) and $KRAS^{G12V}$ (pancreatic cancer) mutations in single CTCs displayed a strong signal-to-noise ratio.
Figure 9:
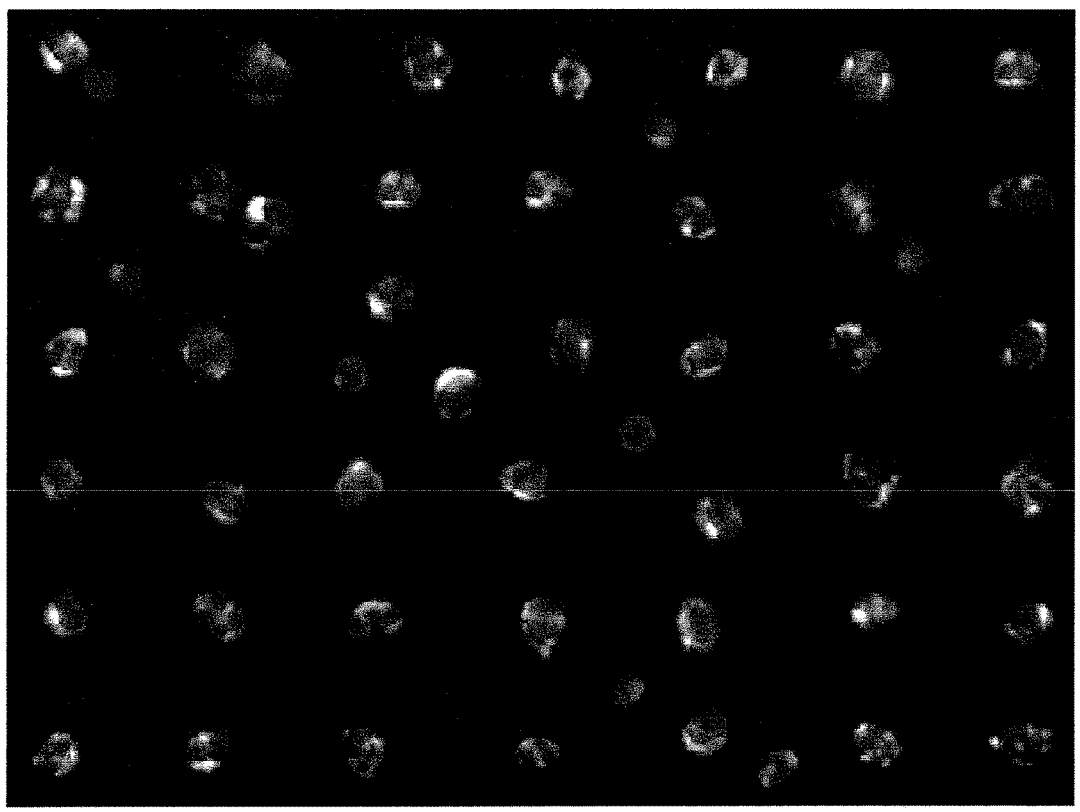
FIG. 9 shows CTCs (red and blue positive) and WBCs (green and blue positive) isolated by NanoVelcro Chips from a cryopreserved PBMC clinical sample collected form a metastatic melanoma patient and preserved in liquid N2 for more than a month. The CTC number isolated form this PBMC sample is very close to that observed from a freshly processed blood sample. In addition, the morphology and fluorescent intensity of the surface markers on these CTCs remains intact for fluorescent immunostaining.
Figures 10A, 10B, 10C:
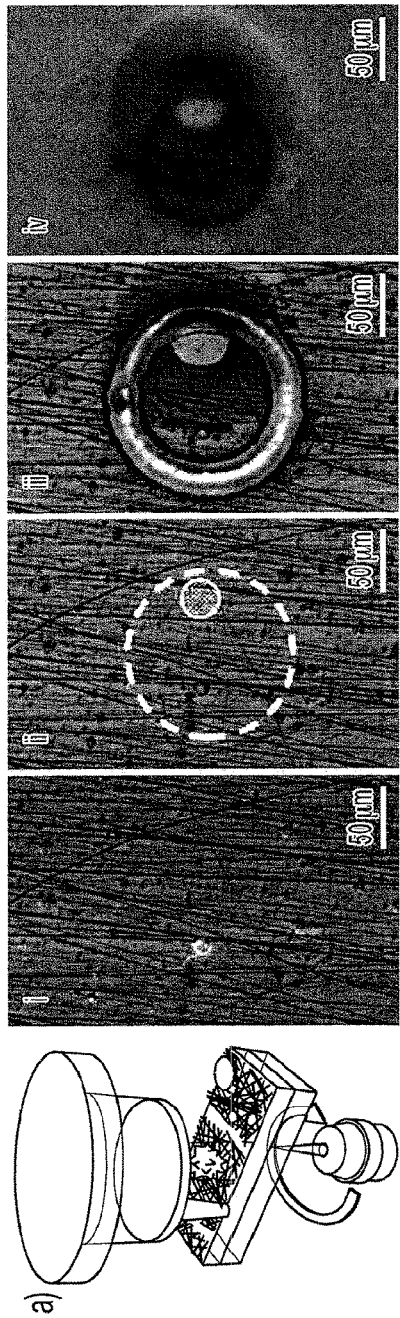
FIGS. 10A-10C show, respectively: a) Micrograph images recording the process of CTC isolation using a ArcturusXT™ Laser Capture Microdissection (LCM) system; i) CTC identification; ii) Determination of IR sticky finger positions and UV dissection route; iii) UV laser dissection; iv) Isolated CTC immobilized on the LCM cap. b) Circos plots representing the coverage areas of Exome-Seq. With each dot indicating a sequenced area among the captured areas by the exome-enrichment kit, the rings from the inside out represent WBC, pooled CTCs, CTC-1 and CTC-2. The outermost ring represents the karyotype of the human reference genome (hg19), with red areas being centromeres. c) The shared mutations between CTCs and WBC are compared with the shared mutations among CTCs. (CTCp=pooled CTCs)

Sequencing point mutations in single CTCs. By using the transparent NanoVelcro substrate approach we were able to isolate 12 single CTCs (without contamination of WBCs) from a melanoma patient, and each CTC was transferred into a 500-µL Eppendorf tube for molecular analyses in sequence. We were able to carry out PCR and exome sequencing on these CTCs to confirm that BRAF$^{v600E}$ mutation and NRAS deletion were present in these single CTCs (FIG. 8). More exciting, these mutations have been observed in biopsy tissue of the same patient.

Methods For Storing Circulating Tumor Cells For Biobanking Applications

Circulating Tumor Cells (CTCs) (Pantel, K. & Alix-Panabieres, C. Circulating tumour cells in cancer patients: challenges and perspectives. *Trends in Molecular Medicine* 16, 398-406 (2010).). The most common causes of cancer-related death in patients occur when solid tumors metastasize. While the molecular mechanisms of cancer metastases are still largely unknown, there is a considerable body of evidence indicating that tumor cells are shed from a primary tumor mass at the earliest stages of malignant progression (Kaiser, J. Medicine. Cancer's circulation problem. *Science* 327, 1072-4 (2010); Bernards, R. & Weinberg, R. A. A progression puzzle. *Nature* 418, 823 (2002); Criscitiello, C., Sotiriou, C. & Ignatiadis, M. Circulating tumor cells and emerging blood biomarkers in breast cancer. *Current Opinion in Oncology* 22, 552-8 (2010)). These 'break-away' cancer cells enter the blood stream and travel to different tissues of the body as the cellular origin of metastases (Pantel, K. & Brakenhoff, R. H. Dissecting the metastatic cascade. *Nature Reviews Cancer* 4, 448-56 (2004)). The cells that escape from the primary tumor are known as CTCs. The gold standard for determining tumor status is through the histopathology analysis of biopsy samples. In early stage metastasis or recurrence, it is difficult to identify the metastatic/recurrence sites for biopsy.

CTCs can be regarded as the "liquid biopsy" of the tumor, thus providing convenient access to tumor cells, and earlier access to potentially fatal metastases. However, detection and characterization of CTCs have been technically challenging due to the extremely low abundance (a few to hundreds per mL) of CTCs among a high number ($10^9$ cells/mL) of hematologic cells (Racila, E., Euhus, D., Weiss, A. J., Rao, C., McConnell, J., Terstappen, L. W. M. M. & Uhr, J. W. Detection and characterization of carcinoma cells in the blood. *Proceedings of the National Academy of Sciences of the United States of America* 95, 4589-4594 (1998); Zieglschmid, V., Hollmann, C. & Bocher, O. Detection of disseminated tumor cells in peripheral blood. *Critical Reviews in Clinical Laboratory Sciences* 42, 155-96 (2005)). It has been established that the variation of CTC number over the course of treatment period was found to be an independent predictor of therapeutic outcomes, progression-free and overall survival (Tan, S. J., Yobas, L., Lee, G. Y., Ong, C. N. & Lim, C. T. Microdevice for the isolation and enumeration of cancer cells from blood. *Biomedical Microdevices* 11, 883-92 (2009)) of solid-tumor patients. Further, molecular analyses of these CTCs found in cancer patients may yield critical genomic, proteomic, or metabolomic information that could steer effective treatment of the cancer patient. CTCs can be obtained from peripheral blood constitute a convenient and minimally invasive approach for recording different stages of cancer progressions that could help to better understand disease development and facilitate the development of new treatment approaches. If CTC can be collected and preserved in a CTC bank, it can allow researchers to retrospectively analyze CTCs at different evolutionary stages of the disease.

Many Tissue banking approaches have been established but there is no such protocol and concept demonstrated for CTCs.

An embodiment of the current invention preserves circulating tumor cells (CTCs) and is minimally invasive as it only requires a blood draw from the cancer patient. Access to the CTCs can provide a window into the state of the tumor mass, negating the need to perform a biopsy. Thus, it is possible to dynamically record a tumor's progression/evolution by collecting these CTCs from the patient over the course of treatment. Ideally, a thorough understanding and knowledge of how a tumor has evolved resistance to a drug, at the genetic/transcription level, can provide insight into the design of better drugs to inhibit cancer proliferation.

CTCs are present in blood samples collected from cancer patients. The most straightforward approach to banking CTCs is to bank the whole blood. However, routine blood storage is limited to 21 days at 1-6 ° C. when treated with acid-citrate-dextrose (ACD), citrate-phosphate-dextrose (CPD) or citrate-phosphate-double dextrose (CP2D). This can be extended to 35 days when treated with citrate-phosphate-dextrose-adenine (CPDA1) (5 weeks for WBC, 6 weeks for RBC), and also involves refrigeration. Also, of concern is that WBCs could attack CTCs, leading to a short lifetime for CTCs. Long-term storage of whole blood is relatively uncommon, and requires additives and solvents that may disrupt the viability of CTCs in these samples.

Banking CTCs, according to an embodiment of the current invention, removes serum and RBC and collects peripheral blood mononuclear cells (PBMC) for cryopreservation. Currently, we have established three different protocols for cryopreservation of CTCs.

Ficoll Paque Method:
1. Dilute the whole blood with 2× the volume with buffer.
2. Carefully layer the diluted cell suspension over 15 mL of Ficoll-Paque in a 50 mL conical tube.
3. Centrifuge at 400×g for 30-40 minutes at RT.
4. Aspirate the upper layer leaving the mononuclear cell layer undisturbed at the interphase.
5. Carefully transfer the mononuclear cell layer to a new conical tube.
6. Fill conical tube with buffer, mix, and centrifuge at 300×g for 10 minutes at RT. Remove supernatant.
7. Finally, resuspend cells in a mixture of culture media and 10% DMSO and place in liquid N2.

Buffy Coat Method:
1. Dilute the whole blood with 2× the volume with buffer.
2. Carefully layer the diluted cell suspension over a small volume of a high-density solution (ie., sucrose, cesium chloride) in a 50 mL conical tube.
3. Spin the diluted whole blood sample at 200×g for 10 minutes at room temperature.
4. Remove the concentrated leukocyte band.
5. Carefully transfer the mononuclear cell layer to a new conical tube.
6. Fill conical tube with buffer, mix, and centrifuge at 300×g for 10 minutes at RT. Remove supernatant.
7. Finally, resuspend cells in a mixture of culture media and 10% DMSO and place in liquid $N_2$.

Red Blood Cell Lysis:
1. Dilute the whole blood with 1× the volume of red blood cell lysis buffer.
2. Spin the whole blood solution at 300×g for 10 minutes at room temperature. Remove supernatant.
3. Resuspend the cells with buffer, mix, and centrifuge at 300×g for 10 minutes at RT. Remove supernatant.
4. Finally, resuspend cells in a mixture of culture media and 10% DMSO and place in liquid $N_2$.

CTCs integrity remained unchanged after Cryopreservation. The PBMC samples preserved under the above mentioned protocols can be subjected for CTC enrichment approaches using a CTC enrichment technology (e.g., NanoVelcro Chips, see H.-R. Tseng, S. Wang, H. Wang, K. Liu (2010) Microfluidic Lab-on-a-Chip Device for Capturing Circulating Tumor Cells, and Use for Diagnosis of Metastatic Cancer. PCT Int. Appl. WO 2010108003, the entire content of which is incorporated herein by reference) or by the methods above.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for isolating preselected cell types from a fluid sample comprising a plurality of cell types, said system comprising:
   a cell-capture fluidic chip; and
   chip holder configured to receive said cell-capture fluidic chip and to maintain said cell capture fluidic chip with a substantially fluid-tight seal while in operation,
   wherein said chip holder is further configured to release said cell-capture fluidic chip to be removed from said chip holder for further processing,
   wherein said cell-capture fluidic chip comprises:
   a substrate,
   a laser micro-dissection membrane configured for laser micro-dissection disposed on said substrate, and a channel-defining layer disposed on said laser micro-dissection membrane,
wherein said laser micro-dissection membrane has a surface comprising at least one of a structural or a chemical modification to capture said preselected cell types preferentially over other cell types of said plurality of cell types,
wherein said channel-defining layer is removable from said laser micro-dissection membrane for further processing of said cell-capture fluidic chip, and
wherein said cell-capture fluidic chip has an input port to receive fluid from a fluid source and an output port to expel processed fluid such that said fluid sample flows from said fluid source through a fluid channel defined by said channel-defining layer over at least a portion of said surface of said laser micro-dissection membrane while in operation.

2. The system for isolating preselected cell types according to claim 1, wherein said channel-defining layer defines said fluid channel such that at least a portion of said fluid channel has a surface structure to cause chaotic mixing resulting from at least partially turbulent flow.

3. The system for isolating preselected cell types according to claim 1, wherein said surface of said laser micro-dissection membrane comprises said chemical modification to capture said preselected cell types preferentially over other cell types of said plurality of cell types, and
wherein said preselected cell types are circulating tumor cells.

4. The system for isolating preselected cell types according to claim 3, wherein said chemical modification of surface of said laser micro-dissection membrane comprises a polymer.

5. The system for isolating preselected cell types according to claim 4, wherein said polymer of said surface of said laser micro-dissection membrane comprises at least one of Poly(Lactic-co-Glycolic Acid) (PLGA), PolyCaproLactone (PCL), PolyLactide (PLA) or Chitosan (Poly-(D)glucosamine).

6. The system for isolating preselected cell types according to claim 5, wherein said polymer further comprises polyethylene glycol (PEG).

7. The system for isolating preselected cell types according to claim 4, wherein said polymer is at least partially formed into nano fibers.

8. The system for isolating preselected cell types according to claim 5, wherein said polymer is at least partially formed into nano fibers.

9. The system for isolating preselected cell types according to claim 8, wherein said polymer further comprises a circulating tumor cell capture agent attached thereto by at least one of biotin or streptavidin conjugation.

10. The system for isolating preselected cell types according to claim 9, wherein said circulating tumor cell capture agent comprises at least one of EpCAM, CA19-9, CD146, or CD147 antibodies.

11. The system for isolating preselected cell types according to claim 1, wherein said surface of said laser micro-dissection membrane comprises a chemical modification to capture fetal nucleated red blood cells from maternal blood preferentially over other cell types of said plurality of cell types.

12. The system for isolating preselected cell types according to claim 11, wherein said chemical modification comprises at least CD71 and CD 147antibodies attached to said surface of said laser micro-dissection membrane.

13. The system for isolating preselected cell types according to claim 1, further comprising a laser that has a wavelength and power to cut said laser micro-dissection membrane at selected sections thereof to remove selected portions of said laser micro-dissection membrane for further processing.

14. The system for isolating preselected cell types according to claim 13, wherein said laser is an ultraviolet laser.

15. The system for isolating preselected cell types according to claim 14, further comprising an infrared laser and an infrared sensitive adhesion element,
wherein said infrared sensitive adhesion element is adapted to be arranged proximate a laser dissected portion of said laser micro-dissection membrane such that said infrared sensitive adhesion element adheres thereto to facilitate removal of said laser dissected portion.

16. A cell-capture fluidic chip for capturing preselected cell types from a fluid sample comprising a plurality of cell types, the cell-capture fluidic chip comprising:
a substrate;
a laser micro-dissection membrane configured for laser micro-dissection disposed on said substrate; and
a channel-defining layer disposed on said laser micro-dissection membrane,
wherein said laser micro-dissection membrane has a surface comprising at least one of a structural or a chemical modification to capture said preselected cell types preferentially over other cell types of said plurality of cell types,
wherein said channel-defining layer is removable from said laser micro-dissection membrane for further processing of said cell-capture fluidic chip, and
wherein said cell capture fluidic chip has an input port to receive fluid from a fluid source and an output port to expel processed fluid such that said fluid sample flows from said fluid source through a fluid channel defined by said channel-defining layer over at least a portion of said surface of said laser micro-dissection membrane while in operation.

17. The cell-capture fluidic chip according to claim 16, wherein said channel-defining layer defines said fluid channel such that at least a portion of said fluid channel has a surface structure to cause chaotic mixing resulting from at least partially turbulent flow.

18. The cell-capture fluidic chip according to claim 16, wherein said surface of said laser micro-dissection membrane comprises said chemical modification to capture said preselected cell types preferentially over other cell types of said plurality of cell types, and
wherein said preselected cell types are circulating tumor cells.

19. The cell-capture fluidic chip according to claim 18, wherein said surface of said chemical modification of said surface of said laser micro-dissection membrane comprises a polymer.

20. The cell-capture fluidic chip according to claim 19, wherein said polymer of said surface of said laser micro-dissection membrane comprises at least one of Poly(Lactic-co-Glycolic Acid) (PLGA), PolyCaproLactone (PCL), PolyLactide (PLA) or Chitosan (Poly-(D)glucosamine).

21. The cell-capture fluidic chip according to claim 20, wherein said polymer further comprises polyethylene glycol (PEG).

22. The cell-capture fluidic chip according to claim 19, wherein said polymer is at least partially formed into nanofibers.

23. The cell-capture fluidic chip according to claim 20, wherein said polymer is at least partially formed into nanofibers.

24. The cell-capture fluidic chip according to claim 23, wherein said polymer further comprises a circulating tumor cell capture agent attached thereto by at least one of biotin or streptavidin conjugation.

25. The cell-capture fluidic chip according to claim 24, wherein said circulating tumor cell capture agent comprises at least one of EpCAM, CA19-9, CD146, or CD147 antibodies.

26. The cell-capture fluidic chip according to claim 16, wherein said surface of said laser micro-dissection membrane comprises said chemical modification, and
    wherein said preselected cell types are fetal nucleated red blood cells from maternal blood.

27. The cell-capture fluidic chip according to claim 26, wherein said chemical modification comprises at least CD71 and CD 147 antibodies attached to said surface of said laser microdissection membrane.

28. A method of isolating preselected cell types from a fluid sample comprising a plurality of cell types, comprising:
    providing a cell-capture fluidic chip, comprising:
        a substrate,
        a laser micro-dissection membrane configured for laser micro-dissection disposed on said substrate, and
        a channel-defining layer disposed on said laser micro-dissection membrane;
    providing said fluid sample such that it flows through a fluid channel defined by said channel-defining layer over at least a portion of said surface of said laser micro-dissection membrane to capture said preselected cell types from said fluid sample;
    removing said channel-defining layer from said laser micro-dissection membrane and said substrate of said cell-capture fluidic chip after said providing said fluid sample; and
    performing laser micro-dissection on said laser micro-dissection membrane and said substrate of said cell-capture fluidic chip after said removing said channel-defining layer to collect said preselected cell types captured from said fluid sample,
    wherein said laser micro-dissection membrane has a surface comprising at least one of a structural or a chemical modification to capture said preselected cell types preferentially over other cell types of said plurality of cell types,
    wherein said channel-defining layer is removable from said laser micro-dissection membrane for further processing of said cell-capture fluidic chip, and
    wherein said cell-capture fluidic chip has an input port to receive said fluid sample from a fluid source and an output port to expel processed fluid such that said fluid sample flows from said fluid source through a fluid channel defined by said channel-defining layer over at least a portion of said surface of said laser micro-dissection membrane while in operation.

29. The method of isolating preselected cell types according to claim 28, wherein said performing laser micro-dissection comprises directing an ultraviolet laser onto said laser micro-dissection membrane to selectively cut off section of said laser micro-dissection membrane that have preselected cell types attached thereto.

* * * * *